United States Patent [19]

Kolobow et al.

[11] Patent Number: 4,551,251

[45] Date of Patent: Nov. 5, 1985

[54] MONOLITHIC INTEGRATED FLOW CIRCUIT

[75] Inventors: Theodor Kolobow, Rockville; Yoichiro Ito, Bethesda, both of Md.

[73] Assignee: The United States of America as represented by the Department of Health and Human Services, Washington, D.C.

[21] Appl. No.: 587,682

[22] Filed: Mar. 6, 1984

[51] Int. Cl.[4] .............................................. B01N 15/08
[52] U.S. Cl. .................................. 210/635; 210/657; 210/198.2
[58] Field of Search ............ 210/656, 657, 658, 198.2, 210/198.3, 635; 55/386

[56] References Cited

U.S. PATENT DOCUMENTS

| | | |
|---|---|---|
| 3,149,941 | 9/1964 | Barnitz et al. .................... 55/386 |
| 3,230,167 | 1/1966 | Golay . |
| 3,399,972 | 9/1968 | Skeggs et al. . |
| 3,465,884 | 9/1969 | Matherne, Jr. . |
| 3,493,497 | 2/1970 | Pretorius et al. . |
| 3,503,712 | 3/1970 | Sussman . |
| 3,522,172 | 7/1970 | Pretorius et al. . |
| 3,598,728 | 8/1971 | Bixler et al. . |
| 3,775,309 | 11/1973 | Ito et al. . |
| 3,782,078 | 1/1974 | Jerpe ........................... 55/386 |
| 3,784,467 | 1/1974 | Tanimura et al. . |
| 3,796,657 | 3/1974 | Pretorius et al. . |
| 3,853,765 | 12/1974 | Tanimura et al. . |
| 3,856,681 | 12/1974 | Huber . |
| 4,051,025 | 9/1977 | Ito . |
| 4,116,836 | 9/1978 | DeAngelis ..................... 55/386 |
| 4,139,458 | 2/1979 | Harrison ....................... 210/657 |
| 4,207,188 | 6/1980 | Tsuda et al. . |
| 4,208,284 | 6/1980 | Pretorius et al. . |

OTHER PUBLICATIONS

Journal of Chromatographic Science, vol. 8, Jun. 1970, pp. 315-322, "Countercurrent Chromatography . . . Solid Support".

Primary Examiner—John Adee
Attorney, Agent, or Firm—Browdy and Neimark

[57] ABSTRACT

A monolithic multi-channel integrated flow circuit comprising a support matrix sheet or plate impressed or embossed with the desired circuitry; the desired circuit elements such as transfer conduit and separation columns are integral with and defined by the support matrix, which conveniently comprises a first deformable support sheet embossed with the circuits elements by thermoforming techniques, and bonded to a support blank or correspondingly embossed second support sheet to complete and define the circuit.

18 Claims, 18 Drawing Figures

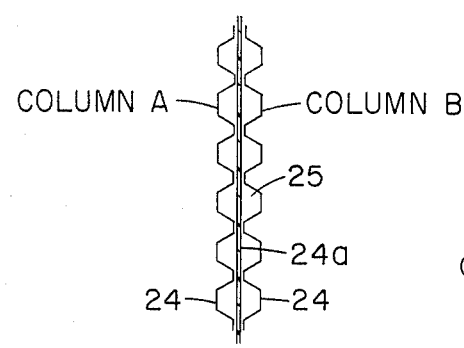 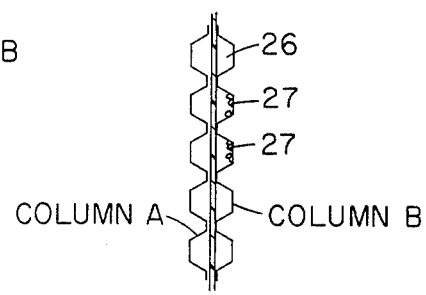
FIGURE 9a  FIGURE 9b
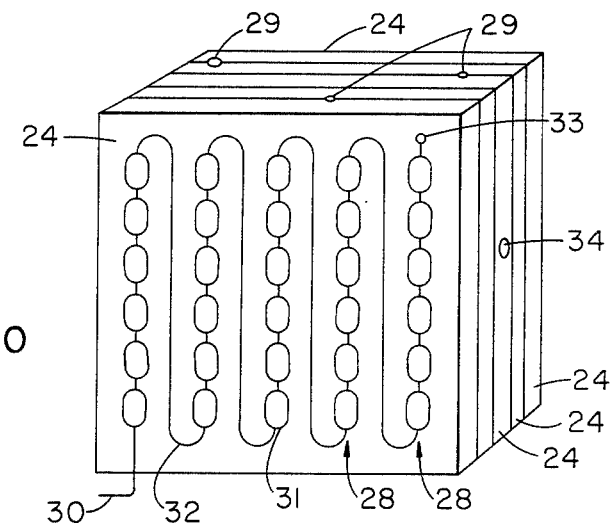
FIGURE 10
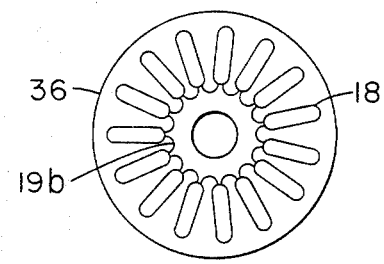
FIGURE 12
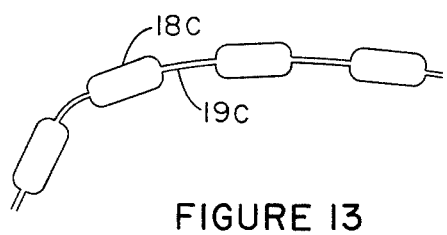
FIGURE 13

MONOLITHIC INTEGRATED FLOW CIRCUIT

Field of the Invention

The invention relates to monolithic integrated flow circuits useful in a variety of analytical and preparative applications, and particularly relates to chromatographic flow circuits adaptable to a broad spectrum of known chromatographic separation and concentration processes, including liquid partition chromatography, liquid-solid chromatography, ion-exchange chromatography, gas-liquid chromatography, and gas-solid chromatography.

Background of the Invention

In the field of separation science and analytical chemistry, tubing is extensively used to transfer gases and liquids in a closed space. Conventional columns for droplet counter-current chromatography (CCC) are made of multiple tubular units interconnected with narrow-bore transfer tubing, as described, for example, in U.S. Pat. No. 3,784,467 issued Jan. 8, 1974 to Tanimura et al. A typical circuit has one hundred or more units and therefore requires hundreds of junctions between the column units, each junction is a potential source of leakage and failure. Columns for locular CCC are prepared by manually spacing multiple centrally perforated partitions into a tubular column at regular intervals. Although the method yields efficient separation, column preparation requires much tedious work which limits the practical use of the method. Centrifugal CCC and cell elutration methods typically use a coiled tube circumferentially placed at the periphery of a rotor so that each helical turn retains the stationary phase for partitioning, and also subjects cells to counter-flow of the solvent for elutriation (see, e.g. U.S. Pat. Nos. 3,775,309 and 4,051,025, issued to Ito et al Nov. 27, 1973 and Sept. 27, 1977, respectively). The helical column configuration, however, is found to have shortcomings, as the retention of the stationary phrase and mixing of the two phases are not satisfactory for viscous polymer phrase systems; and in cell elutriation the column forms a dead space where cells stay but without separation. Improvements are not easy to attain by simple changes of the helical configuration of tubing.

These drawbacks in chromatographic apparatus, especially in CCC and cell elutriation with conventional columns, can be overcome by utilizing chromatographic separation columns according to the present invention with a suitable flow circuit pattern.

Summary of the Invention

The invention comprises a monolithic multi-channel integrated flow circuit (MIFC) for circulating fluids. For partitioning fluids according to conventional chromatograhic principles, the flow circuit of the invention includes a plurality of separation columns or channels interconnected in series by integrated narrower-bore transfer conduits for delivering fluid from one column to a next successive column. The MIFC of the invention comprises a support matrix or sheet impressed with the desired circuitry by appropriate molding or machining techniques; the circuitry is thus integral with and at least partially defined by the support matrix. Conveniently, the circuit is fabricated by embossing the circuit in a thin-gauge metal or plastic support sheet, followed by bonding of the embossed sheet to a support sheet blank to define the circuit, according to well-known thermoforming techniques, such as those used for blister packaging. Very complicated integrated flow circuits can thus readily be produced according to desired pattern in a compact sheet without prior art adaptors, transfer tubing, joints, and other discrete elements requiring assembly and structural integrity. Either flexible matrix sheets, or thicker, more rigid matrix sheets (herein referred to as matrix "plates") may be employed.

Brief Description of the Drawing

In the Drawing:

FIG. 1b. schematically illustrates a DCCC System including a DCCC MIFC similar to FIG. 1a;

FIG. 2(a—c) schematically illustrates a process for molding the MIFC of FIG. 1a;

FIG. 9a is a front view of a separation column in a MIFC circuit having an internal separating partition or membrane;

FIG. 9b is a front view of the separation column of FIG. 9a, wherein an MIFC is used to supply isolated compartments;

FIG. 10 is a block MIFC unit;

FIG. 11 is a graph of a DNP amino acid separation effected with the MIFC of FIG. 6a;

FIG. 12 is a toroidal MIFC unit; and

FIG. 13 is a tubular MIFC unit comprising portions of varying diameter, illustrated partially coiled for use.

DETAILED DESCRIPTION OF THE INVENTION

According to the present invention, many complex flow patterns are obtainable from plastic support sheets or similar matrix material molded to define the monolithic integrated flow circuits (MIFC) herein described. Characteristic features of MIFC are as follows:

1. Complex patterns of either single or multiple flow channels are defined in a compact sheet without interconnection of discrete elements.

2. MIFC is inexpensive to make and can thus be disposable.

3. Various matrix materials can be chosen according to chemical resistance, biocompatibility, transparency, or other characteristics.

Figure 1B:
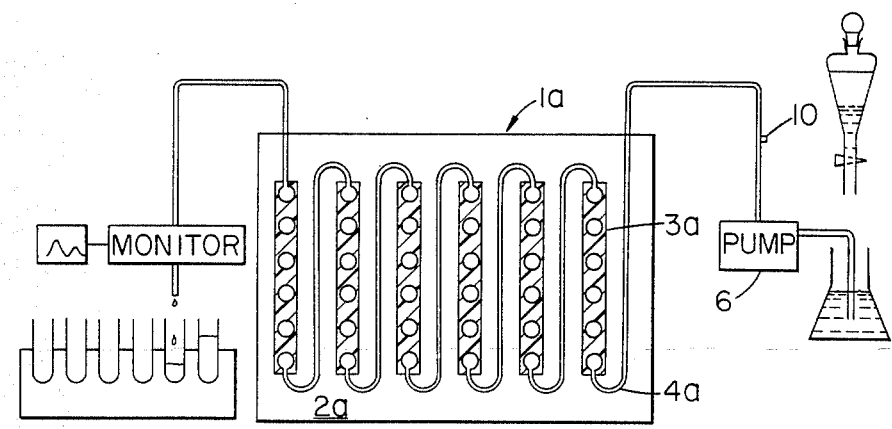
Figure 1A:
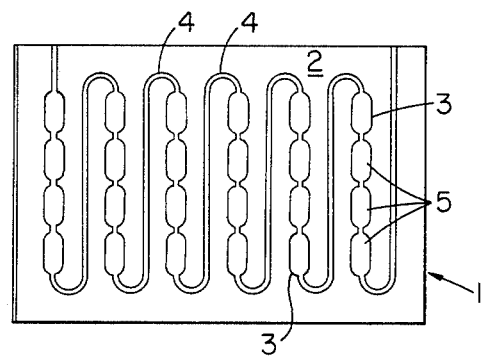
FIG. 1a is a plan view of a MIFC according to the invention particularly useful for DCCC.

With particular reference to FIG. 1a illustrates an MIFC according to the invention, wherein an integrated flow circuit indicated generally at 1 is defined by a pair of corresponding formed plastic matrix sheets 2. The circuit 1 is particularly adapted for droplet counter current chromatography, and includes a plurality of separation columns 3 disposed in series with integrated transfer conduits 4 communicating the columns 3. Each of the columns 3 is illustrated as having a series of constrictions defining a plurality of locules 5; however, the shape of the columns 3 is varied as applicable. An alternate series of columns 3a is illustrated in FIG. 1b, wherein an integrated flow circuit 1a formed in matrix 2a having transfer conduits 4a communicating columns 3a is shown in a droplet CCC system. In operation, the flow circuit 1a is held substantially in the vertical position and is filled with a preequilibrated two-phase solvent system (stationary phase) having the requisite affinity for the column wall. The sample solution is injected into a column 3a through a port 5 located between the outlet of a pump and the inlet of the circuit 1a and elution proceeds with the mobile phase. When the stationary phase is the lower (upper) phase, the moblie phase and the sample solutions are introduced through the bottom (top) of each column unit 3a so that the droplets of the mobile phase can move toward the other end of the column unit by the effect of gravity. This mode of elution forms multiple droplets of the mobile phase which divide the space of each column unit 3a into numerous units. Consequently, solutes in the sample solution are efficiently partitioned between the moving droplets and the surrounding stationary phase, resulting in chromatographic separation of the solutes according to their partion coefficients. By dividing each column unit 3a into several subunits as shown in FIG. 1a, a substantially higher partition efficiency is obtained. As described infra, droplet CCC can be performed under an enhanced acceleration field by centrifugation. Under a strong centrifugal force field, the flow rate of the mobile phase can be greatly increased without loss of partition efficiency and, in addition, either aqueous or nonaqueous phases can be used as the mobile phase.

Figure 2A:
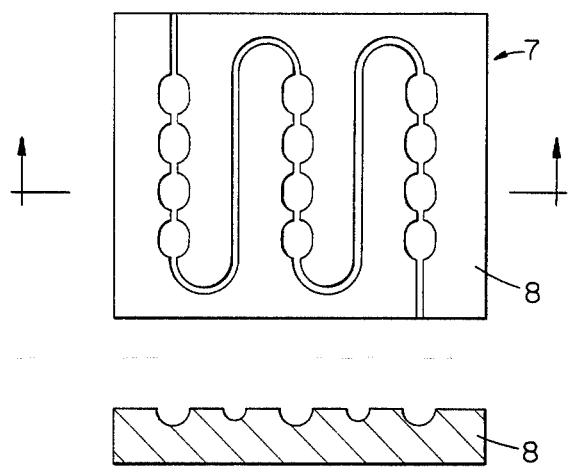
Figure 2B:
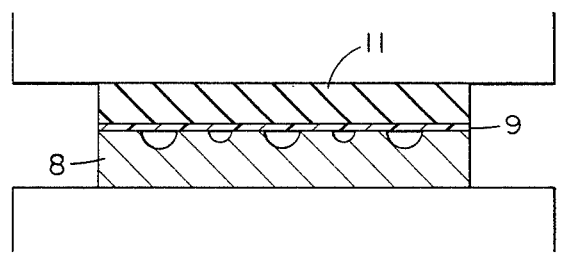
Figure 2C:
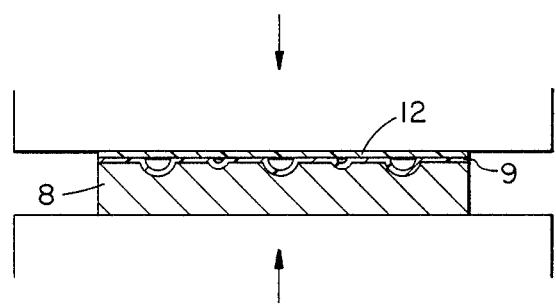

The MIFC of FIG. 1 is conveniently fabricated as illustrated in FIGS. 2a–c, wherein the desired pattern of a flow circuit 7 is first machined from a metal plate 8, typically an aluminum plate, (FIG. 2a), using a numerically controlled milling machine; a suitable thin-gauge plastic sheet 9 such as polypropylene is positioned over the molding plate, and a thick rubber pressure pad 11, usually silicone rubber sheet, is placed over the plastic sheet. The mold is then sandwiched between a pair of temperature controlled plates, and the plastic sheet conformed to the mold. Under proper temperature and pressure the rubber sheet pushes the plastic sheet into the voids of the mold, and the plastic sheet thus assumes the contours of the mold. With some polymers, the temperature of the mold will then have to be raised to anneal the formed sheet, to prevent significant deformation changes during the fusion. Following this, the mold is cooled while pressure is still applied, and the formed parts are removed. The plastic sheet 9 may be vacuum-formed rather than pressure-formed, as is well-known in the art. As shown in FIG. 2c, the thermoformed plastic sheet 9 is then fused to a flat plastic sheet 12 at appropriate temperatures and pressures while still in the original molding plate, and then cooled. The thermoformed plastic sheet 9 may be fused to an unformed (flat) plastic sheet to define the flow circuit 7, or the plastic sheet 9 may be fused to a corresponding, formed plastic sheet (not illustrated) to define the circuit 7.

Other molding techniques such as injection molding and transfer molding are also generally useful in fabricating MIFC according to the invention; with other molding techniques, fabrication of a flow circuit integral with a single sheet is contemplated.

Figure 3:
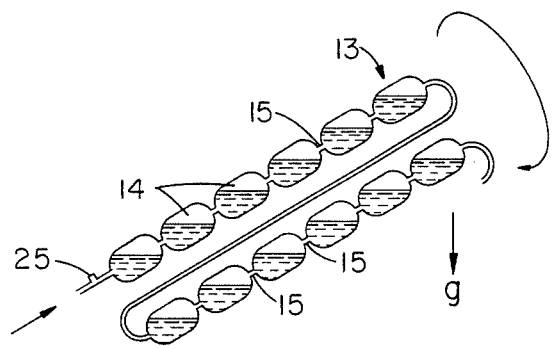
FIG. 3 is a plan view of a MIFC according to the invention useful in rotation locular CCC.

For locular CCC a pair of molded plastic sheets (each being the mirror image of the other) is fused or bonded to form multiple cylindrical compartments or chambers (locules) which are connected in series with narrow-bore transfer channels. The principle of locular CCC is schematically illustrated in FIG. 3. A MIFC circuit 13 having locules 14 communicating via transfer channels 15 mounted on a rotary holder (not shown) is first filled with the stationary phase (either aqueous or organic) and the sample solution is injected through a sample port 25. The holder is rotated around its inclined axis while the mobile phase is eluted through the column. As in droplet CCC, when the lower (upper) phase is stationary, the sample solution and the mobile phase are introduced through the bottom (top) of the column unit. With this elution mode, each locular space is filled with nearly equal volumes of the two phases, forming a horizontal interface while rotation produces efficient mixing of the two phases at the interface. Consequently, solutes are effectively partitioned between the two phases in each locule and chromatographically separated according to their partition coefficients. This scheme is particularly useful for preparative-scale separations.

Figure 4:
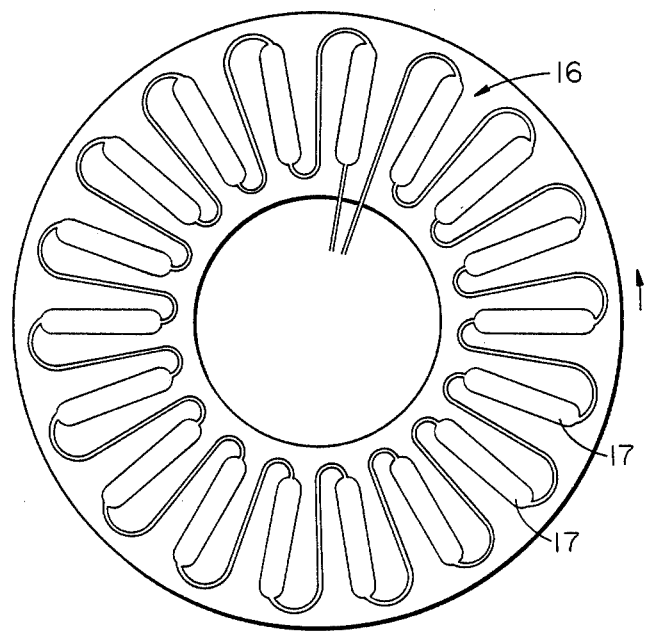
FIG. 4 illustrates a toroidal MIFC according to the invention for centrifugal partitioning.

As mentioned supra, droplet CCC can be performed under a centrifugal force field. FIG. 4 shows an exemplary MIFC circuit 16 for centrifugal droplet CCC. The doughnut shaped (toroidal) circuit 16 consists of multiple column units 17 radially arranged around the periphery of a centrifuge rotor so that centrifugal force effectively accelerates the motion of the droplets. When the lower (upper) phase is stationary, the mobile phase is introduced from the distal (proximal) end of the column unit to facilitate retention of the stationary phase. The partition efficiency can be increased by dividing each column unit into many locules or subunits, as in FIG. 1a.

Figure 5:
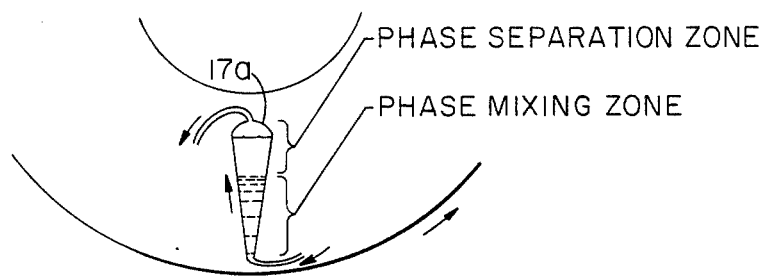
FIG. 5 is a detail illustration of a tapered separation column design for use with the MIFC of FIG. 4.

For application to viscous polymer phase systems, the shape of the column units 17 can be modified to taper off toward the peripheral end as shown at 17a in FIG. 5. The poly (ethylene glycol)-rich upper phase introduced from the tapered peripheral end of the column unit 17a is efficiently mixed with the dextran-rich lower stationary phase at the peripheral portion where the linear velocity of the flow is greatest. However, in the proximal portion of the column unit 17a where the linear flow rate is slower, the two phases are completely separated, and only the upper mobile phase is transferred to the next column unit. Thus, this scheme can improve the retention of the stationary phase while providing efficient mixing to promote the partitioning process.

The same tapered column 17a can be efficiently used for particle elutriation. The column 17a is first filled with a single solvent such as water or isotonic saline solution and the particle mixture is introduced from the distal terminal of the column unit. Then the column is eluted with the same solvent while the apparatus is run at a high revolutional speed to produce a strong centrifugal force field. Under a continous flow the particles are subjected to a counteracting centrifugal force field and separated according to size and relative density. Because of the tapered configuration of the column unit, particles are subjected to a high linear flow in the distal portion of the column and quickly enter the middle portion of the column unit where the elutriation process is most effective. Therefore, the system can eliminate or reduce particle aggregation on the retention of particles in the deadspace of the capillary bed.

Figure 6A:
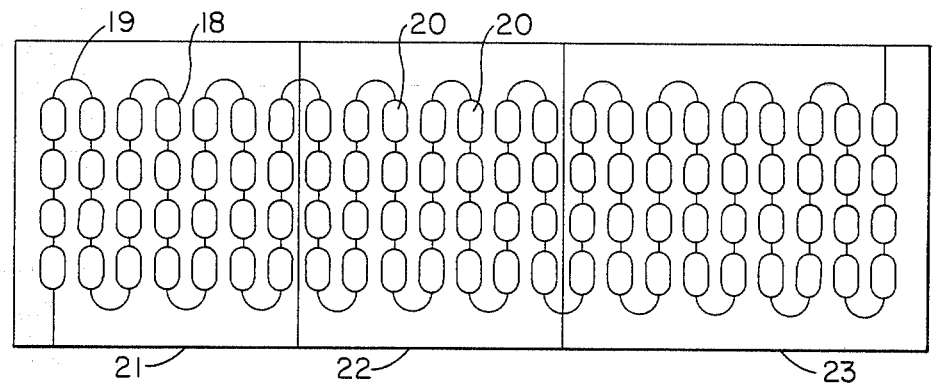
FIG. 6a is a plan view of a plurality of MIFC according to the invention in series communication, including means for preventing build-up of hydrostatic pressure within the circuits.
Figure 6B:
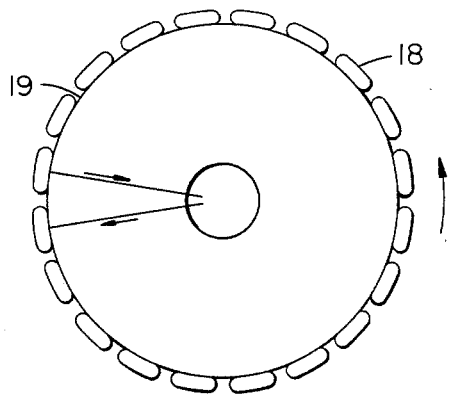
FIG. 6b is the MIFC of FIG. 6a rolled-up to conserve space.
Figure 7:
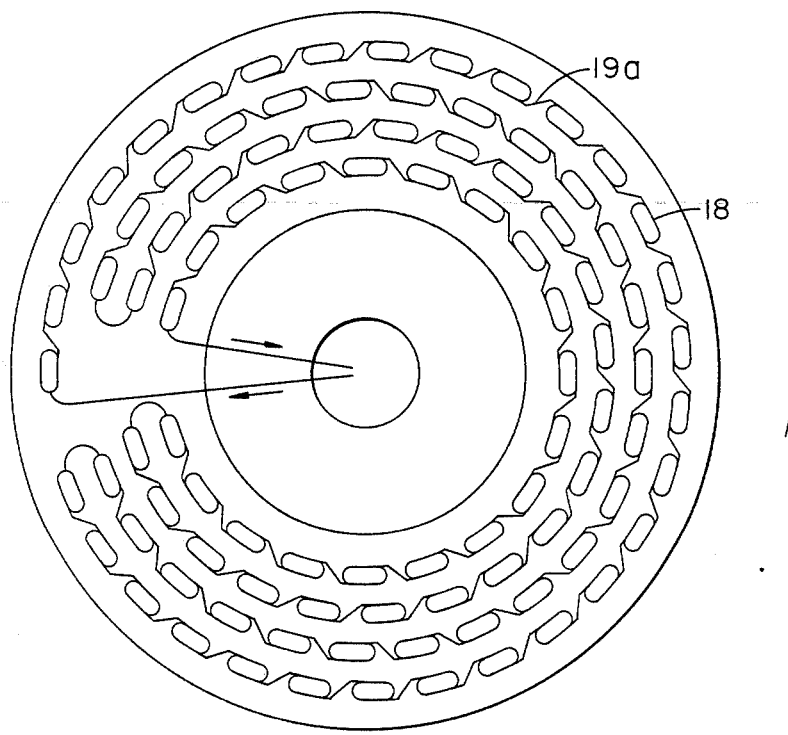
FIG. 7 is a plan illustration of an MIFC series similar to that of FIG. 6a in a toroidal disposition.
Figure 8:
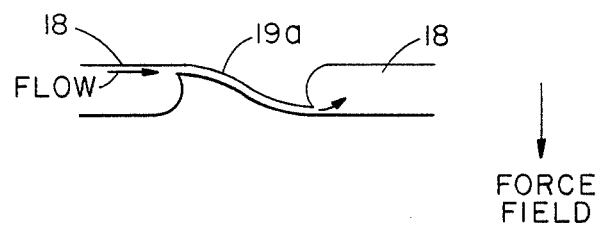
FIG. 8 illustrates a detailed embodiment of an MIFC transfer conduit which promotes mixing.

Theoretically, the efficiency of separation can be increased with the use of multiple plates of MIFC connected in series. The practical limit comes from an accumulated high pressure in the circuit mainly due to hydrostatic forces, especially in centrifugal DCCC using organic/aqueous solvent systems. A signficant decrease of this hydrostatic pressure can be achieved by using the column designs illustrated in FIGS. 6 and 7. In both designs, hydrostatic pressure is reduced by shortening the columns 18; at the same time the liquid drag force is also decreased by shortening the transfer conduits 19 between the columns 18 of the MIFC units 21, 22, and 23. Any decreased mixing effect in the columns 8 may be compensated for by using transfer conduits which produce a jet stream of the mobile phase into the stationary phase in each partition unit, such as the nozzle-shaped transfer conduits 19a illustrated in FIG. 8. The MIFC of FIG. 6a may contain thousands of locules 20 in a typical industrial application; an exemplary laboratory-scale MIFC employed in the separation illustrated in FIG. 11 comprised a sheet of about 10×14 inches containing about 1000 locules 20.

Figure 11:
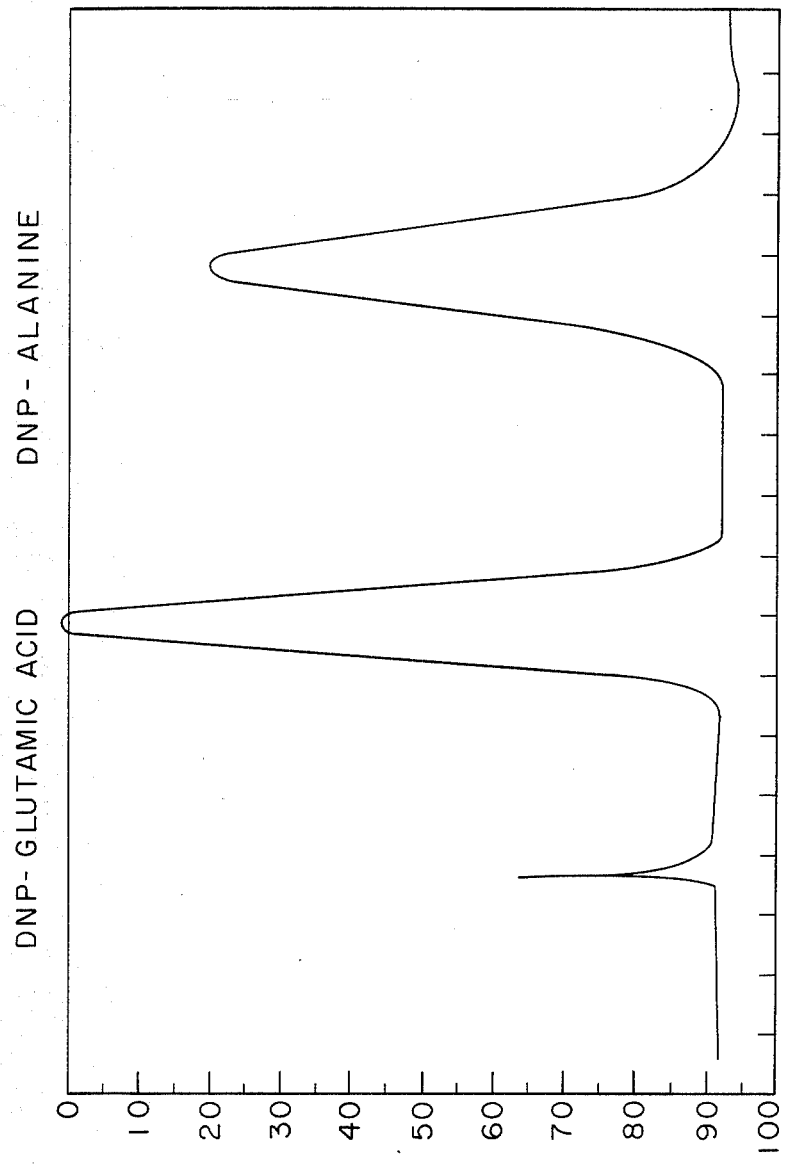

A single MIFC unit can be made of more than two plastic sheets 24 as shown in FIG. 9a. When the middle sheet 24a is a microporous membrane, the unit becomes an efficient dialysis system. As illustrated in FIG. 9b, the locules 25 of Column B in FIG. 9a may be alternatively formed as separate compartments 26 (Column B, FIG. 9b). The compartments 26 may be filled with, for example, cells 27 and a nutrient medium flowed through the circuit of Column A. The compartmentalized cells 27 may then be exposed to experimental substances as desired. FIG. 10 shows a more complex form of MIFC in block shape, with sheets 24 stacked or fused into one single unit. In accordance with this embodiment, a doughnut-shaped MIFC can be used for centrifugal application. As illustrated in FIG. 10, circuits 28 are provided with inlets and outlets 29 for introducing or removing components; a sample inlet is shown at 30. The circuits 28 including columns 31 and conduits 32 on each sheet 24 are interconnected at interconnections 33 in series through the MIFC block. An observation port 34 is included. FIG. 11 is a graph illustrating the separation of DNP amino acids (glutamic acid and alanine) employing the MIFC of FIG. 6a. FIG. 12 is an MIFC unit wherein the columns 18 are toroidally disposed on a support 36, and placed in series communication by shortened transfer conduit 19b.

The MIFC units of the invention may be formed from a variety of matrix materials, including plastics such as polypropylene and TEFLON, superplastics, and metals, especially materials impermeable to the working fluids. Foils (thin-gauge metal sheets) are especially contemplated. The matrix sheets may be bonded by known techniques including diffusion bonding and electron beam welding. The circuitry may be formed by any appropriate techniques, including thermoforming, injection molding, casting, extrusion, etching, and controlled laser beam machining techniques. While the invention is primarily illustrated in terms of embossed or blister circuitry, integrated circuits according to the invention may be also internally formed in support matrices or sheets. The support matrices can be rolled as necessary, and subjected to any desired mixing or shaking force. The columns may be packed according to known chromatographic procedures, or mixing beads or other material may be disposed in the columns, or in one or more of the locules. As illustrated in FIG. 9, the circuits are additionally useful in a variety of filtration and fluid transfer applications. In addition to the embossed circuitry illustrated in FIGS. 1-12, circuitry comprising a continuous conduit of varying diameter, such as illustrated in FIG. 13, is within the scope of the invention. Such tubing comprises a plurality of columns 18c interconnected by integral transfer conduit 19c of a diameter less than the columns 18c; the flow circuit may be as long as desired, and fabricated by known molding techniques such as extrusion from materials such as those disclosed supra, in particular from standard polyethylene tubing.

It is to be understood that the present invention is not limited to the embodiments disclosed which are illustratively offered and that modifications may be made without departing from the invention.

What is claimed is:

1. A monolithic integrated flow circuit consisting essentially of a deformable matrix plate having a flow circuit formed therein, said deformable matrix plate being of formed plastic or metallic thin-gauge sheets, at least one of said sheets having a pattern formed by embossing thereon, said sheets being bonded together to form said flow pattern, said pattern defining a plurality of locules, each of said locules being joined to an adjacent locule by an integral transfer conduit.

2. The flow circuit of claim 1, wherein said flow circuit is embossed in one of said support sheets and the other of said support sheets is a flat blank.

3. The flow circuit of claim 1, wherein corresponding mirror-image halves of each flow circuit are embossed in each matrix sheet.

4. The flow circuit of claim 1, wherein said plurality of locules are radially disposed on a centrifuge rotor and integral transfer conduit communicate the columns in series.

5. The flow circuit of claim 4, wherein at least some of the locules are tapered.

6. A plurality of monolithic flow circuits according to claim 1, wherein the flow circuits formed in said plates are interconnected in series.

7. The flow circuit of claim 1, wherein the transfer conduit functions as a nozzle to produce a jet stream in the transfer fluid.

8. A plurality of monolithic integrated flow circuits according to claim 1, wherein a plurality of said plates are formed into a block of circuits interconnected in series.

9. The flow circuit of claim 3, wherein the corresponding halves of the circuit are separated by a microporous membrane.

10. The flow circuit of claim 2, wherein the flat blank is a microporous membrane.

11. The flow circuit of claim 10, wherein a cell nutrient fluid is circulated through said circuit.

12. The monolithic integrated flow circuit of claim 1, wherein said support sheets are thin-gauge plastic.

13. The monolithic integrated flow circuit of claim 1, wherein said support sheets are thin-gauge metal.

14. The monolithic integrated flow circuit of claim 1, wherein the flow circuit is embossed in a thermoplastic matrix plate by thermoforming.

15. The flow circuit of claim 1, wherein said deformable matrix is essentially transparent.

16. A method for counter-current chromatography comprising separating a first liquid from a second liquid with which said first liquid is mixed by passing a mixture of said first and second liquid through a monolithic integrated flow circuit consisting essentially of a deformable matrix plate having a flow circuit formed therein, said deformable matrix plate being of formed plastic or metallic thin-gauge sheets, at least one of said sheets having a pattern formed by embossing thereon, said sheets being bonded together to form said flow pattern, said pattern defining a plurality of locules, each of said locules being joined to an adjacent locule by an integral transfer conduit and subjecting said mixture to counter-current chromatography in said column.

17. A method of claim 16 wherein the counter-current chromatography is centrifugal counter-current chromatography.

18. The system of claim 16 wherein the counter-current chromatography is droplet counter-current chromatography.

* * * * *